United States Patent
Drubay et al.

(10) Patent No.: US 11,957,868 B2
(45) Date of Patent: Apr. 16, 2024

(54) MEANS FOR TRANSPORTING PERSONS WITH REDUCED MOBILITY COMPRISING A DEVICE WITH FOR CONNECTING TO ASERUM HOLDER, ASSOCIATED CONNECTING ASSEMBLY

(71) Applicant: INSTITUT GUSTAVE ROUSSY, Villejuif (FR)

(72) Inventors: Damien Drubay, Châtillon (FR); Jean-Marie Nebbak, Orly (FR); Joël Daguet, Vitry sur Seine (FR); Serge Pechard, Saint-Michel sur Orge (FR); Christophe Mas, Vitry sur Seine (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 723 days.

(21) Appl. No.: 17/251,641

(22) PCT Filed: Jun. 14, 2019

(86) PCT No.: PCT/EP2019/065663
§ 371 (c)(1),
(2) Date: Dec. 11, 2020

(87) PCT Pub. No.: WO2019/238917
PCT Pub. Date: Dec. 19, 2019

(65) Prior Publication Data
US 2021/0260278 A1 Aug. 26, 2021

(30) Foreign Application Priority Data
Jun. 14, 2018 (FR) ........................................ 1855238

(51) Int. Cl.
*A61M 5/14* (2006.01)
*A61G 5/10* (2006.01)

(52) U.S. Cl.
CPC ............. *A61M 5/1415* (2013.01); *A61G 5/10* (2013.01); *A61G 2203/78* (2013.01);
(Continued)

(58) Field of Classification Search
CPC ......................... A61M 5/1415; A61M 5/1417
See application file for complete search history.

(56) References Cited

U.S. PATENT DOCUMENTS

| 4,511,157 A | 4/1985 | Wilt et al. |
| 4,572,536 A * | 2/1986 | Doughty .................. A61G 7/05 |
| | | 297/188.2 |

(Continued)

FOREIGN PATENT DOCUMENTS

| EP | 2154382 A1 * | 2/2010 | .......... A61M 5/1415 |
| JP | 2016-016244 A | 2/2016 | |
| WO | WO-2014156519 A1 * | 10/2014 | ............... A61G 5/10 |

OTHER PUBLICATIONS

International Search Report as issued in International Patent Application No. PCT/EP2019/065663, dated Aug. 9, 2019.

*Primary Examiner* — Kevin Hurley
*Assistant Examiner* — Hosam Shabara
(74) *Attorney, Agent, or Firm* — Pillsbury Winthrop Shaw Pittman LLP (57) ABSTRACT

A system for transporting persons with reduced mobility includes a chassis having two lateral cross members, a device for connecting to an IV pole including a rod and a wheeled support attached to an end of the rod, the connection device including an attachment support fixed to the chassis, a coupling element designed to be solidly fixed to the rod, a member for connecting the coupling element to the attachment support, a lateral stop attached to at least one of the cross members, the lateral stop being built and arranged to brace the wheeled support in relation to the chassis and to (Continued)

position the IV pole laterally in relation to the transportation system.

14 Claims, 4 Drawing Sheets

(52) U.S. Cl.
CPC ... *A61G 2203/80* (2013.01); *A61M 2209/082* (2013.01); *A61M 2209/084* (2013.01)

(56) References Cited

U.S. PATENT DOCUMENTS

| | | | |
|---|---|---|---|
| 4,767,131 A | 8/1988 | Springer et al. | |
| 5,355,539 A * | 10/1994 | Boettger | A61G 7/05 |
| | | | 5/503.1 |
| 5,374,074 A * | 12/1994 | Smith | A61G 5/10 |
| | | | D12/131 |
| 5,421,548 A | 6/1995 | Bennett et al. | |
| 7,258,310 B2 * | 8/2007 | Norris | A61G 5/10 |
| | | | 248/125.7 |
| 9,506,487 B1 * | 11/2016 | Merritt | F16B 7/0433 |
| 10,582,981 B2 * | 3/2020 | Childs | A61B 50/26 |
| 2016/0302982 A1 * | 10/2016 | Blankenship | A61M 5/1413 |
| 2019/0195252 A1 * | 6/2019 | Pryor | A61M 5/1415 |

* cited by examiner

MEANS FOR TRANSPORTING PERSONS WITH REDUCED MOBILITY COMPRISING A DEVICE WITH FOR CONNECTING TO ASERUM HOLDER, ASSOCIATED CONNECTING ASSEMBLY

CROSS-REFERENCE TO RELATED APPLICATIONS

This application is the U.S. National Stage of PCT/EP2019/065663, filed Jun. 14, 2019, which in turn claims priority to French patent application number 1855238 filed Jun. 14, 2018. The content of these applications are incorporated herein by reference in their entireties.

TECHNICAL FIELD OF THE INVENTION

The invention relates generally to the field of medical equipment used in particular for transporting a patient.

The invention is more particularly concerned with a means for transporting persons with reduced mobility comprising a device for connection to a serum holder. The invention is also concerned with a connection assembly comprising said transporting means connected to a serum holder.

STATE OF THE ART

Transporting a patient requiring intravenous drug administration can turn out to be difficult for hospital staff. Indeed, it is difficult for a single person to simultaneously push the wheelchair transporting the patient and the serum holder that supports the infusion systems, pumps as well as syringe pumps. In order to circumvent this problem, different drug administration devices are transferred, before each trip, from the patient's serum holder to the wheelchair's serum holder, which is usually located at the back of the wheelchair.

However, such transfer operations are more or less time-consuming depending on the number of devices to be transferred. In addition, they require a check of the infusions after each transfer, and their adjustment if necessary. Moreover, these operations are frequent as they have to be carried out when leaving a service, when returning to the room, but also during examinations or treatments, this for each patient. However, hospital staff are often unavailable, so that a wait in the care units is often observed. In addition, when the number of drug administration devices transferred is too large, there is a risk of the wheelchair tipping backwards. In addition, there is a risk of tearing, falling and breaking during each transfer operation.

SUMMARY OF THE INVENTION

Within this context, the invention aims at overcoming all or part of the drawbacks of the state of the art identified above, by providing a solution for reducing the time and number of operations to be carried out before transporting a patient under infusion.

According to a first aspect, the invention is concerned with a transporting means for persons with reduced mobility comprising a chassis with two side cross members connecting a first assembly of rear wheels to a second assembly of front wheels.

In addition, the transporting means includes a device for connection to a serum holder which comprises a rod and a wheeled support attached to one end of said rod.

In particular, the connection device comprises:

an attachment support attached to the chassis,
a coupling element for being secured to the rod of the serum holder, the coupling element comprising:
    a clamp with a housing adapted to receive the rod and,
    a clamping element adapted to hold the rod in the housing,
a member for connecting the coupling element to the attachment support,
a side stop attached to one of the side cross members of the chassis, the side stop being constructed and arranged to ensure that the wheeled support of the serum holder is locked relative to the chassis and to ensure lateral positioning of the serum holder in relation to the transporting means.

By "serum holder" it is meant a device for suspending drug administration devices, also known as an intravenous holder.

By "chassis" it is meant an assembly, which may be foldable, for supporting, in particular, the wheels, seat and backrest of the transporting means.

The invention according to the first aspect solves the aforementioned problems.

By virtue of the transporting means according to the invention, it is no longer necessary, before transporting a patient, to transfer all the drug administration devices from the patient's serum holder to the serum holder of the transporting means.

Indeed, the patient's serum holder is directly connected and secured to the chassis of the transporting means through the connection device, which considerably reduces the time, number of operations and manipulations to be carried out before transferring a patient. In addition, it is not necessary to check infusions after each transfer and adjust them if necessary, which saves a considerable amount of time and reduces waiting times in care units. In addition, since it is no longer necessary to transfer drug administration devices from one serum holder to another, risks of tearing, falling and breaking are also reduced.

In addition, the side stop enables movements of the serum holder relative to the transporting means to be blocked, thus stabilising and securing the patient's serum holder during trips. In particular, this prevents the serum holder from tipping over when the transporting means is moved. In addition, by attaching the side stop to at least one side cross member of the transporting means, a lateral positioning of the serum holder in relation to the transporting means can be ensured which is safer than positioning at the rear or front of the transporting means. Such an arrangement prevents the person pushing the transporting means from hitting the wheeled support of the serum holder during the trip and ensures good visibility.

In addition, the connection device according to the invention is simple, quick to install and adapts to all types of serum holder. It enhances the autonomy of infused patients, who can be easily walked by a relative or a third party. In addition, it requires few modifications to the existing transporting means for the installation of the connection device.

The transporting means according to the first aspect of the invention may also have one or more of the characteristics below, considered individually or in any technically possible combinations.

According to a non-limiting embodiment, the side stop has a shape and dimensions adapted to lock two branches of the wheeled support of the serum holder.

According to a non-limiting embodiment, the connection member has at least one means for returning the coupling element to the chassis. Thus, when the connection member is not in use, the return means positions the coupling member back to its rest position.

According to a non-limiting embodiment, the connection member includes:
- an axis attached to the clamp of the coupling element, said axis being slidably mounted through said at least one ring of the attachment support,
- a radial stop attached to said axis.

By "radial" it is meant a direction orthogonal to the direction of the axis of the connection member.

According to a non-limiting embodiment, the return means is formed by a compression spring surrounding the axis of the connection member, said compression spring being configured to compress between one end of said at least one ring and the radial stop.

According to a non-limiting embodiment, the coupling element is pivotably mounted relative to the connection member.

According to a non-limiting embodiment, the clamp includes two branches, each with an inner surface, the housing being provided in the inner surface of one of the branches.

According to a non-limiting embodiment, the housing is constructed and arranged to form at least two contact points between the housing and the rod.

According to a non-limiting embodiment, the housing has a "V" shape.

According to a non-limiting embodiment, the transporting means comprises at least one armrest for being attached to the chassis, said at least one armrest being constructed and arranged to ensure that the rod of the serum holder is locked relative to said chassis.

According to a non-limiting embodiment, the connection device includes:
- an additional coupling element attached to the connection member, the additional coupling element being designed to be secured to the rod of an additional serum holder and including:
  - a clamp having a housing adapted to receive a rod of the additional serum holder and,
  - a clamping element suitable adapted to hold the rod of the serum holder in the housing,
- an additional side stop attached to the other side cross member of the chassis, said side stop being constructed and arranged to ensure that a wheeled support attached to one end of the rod of the additional serum holder is locked relative to the chassis and to ensure lateral positioning of the additional serum holder relative to the transporting means.

According to a non-limiting embodiment, the connection device includes an additional armrest attached to the chassis, said additional armrest being constructed and arranged to ensure that the rod of the additional serum holder is locked in relation to said chassis.

According to a non-limiting embodiment, at least one of the two armrests is removable.

According to a non-limiting embodiment, the transporting means is one of the transporting means chosen from the following list:
- a wheelchair,
- a wheeled stretcher,
- a wheeled bed,
- a pram.

According to a second aspect, the invention is concerned with an assembly for connecting a serum holder to a transporting means for persons with reduced mobility according to the first aspect, said connection assembly comprising:
- the transporting means,
- the serum holder comprising a rod and a wheeled support attached to one end of said rod,
- the transporting means being coupled to the serum holder by means of the connection device of said transporting means.

BRIEF DESCRIPTION OF THE FIGURES

Further features and advantages of the invention will appear upon reading the following description, with reference to the appended figures, which illustrate:

in FIG. 1, a front view of an example of a transporting means for persons with reduced mobility according to an embodiment of the invention, when connected to a serum holder, in FIG. 2, a side view of the transporting means illustrated in FIG. 1, in FIG. 3a, the locking of a side stop of the transporting means illustrated in FIG. 1 between two branches of a wheeled support of the serum holder, in FIG. 3b, a front view of the side stop illustrated in FIG. 3a, in FIG. 3c, a top view of the side stop represented in FIG. 3a, in FIG. 4a, the coupling element of the transporting means illustrated in FIG. 1, when coupled to the rod of the serum holder, in FIG. 4b, a top view of the coupling element illustrated in FIG. 4a, in a horizontal position, when not coupled to the rod of the serum holder, in FIG. 5a, a top view of the connection device of the transporting means illustrated in FIG. 1, when attached to the wheelchair chassis, in FIG. 5b, a front view of the connection device illustrated in FIG. 5a, when at rest, in FIG. 5c, a top view of the connection device illustrated in FIG. 5a.

DESCRIPTION OF AT LEAST ONE EMBODIMENT

The invention is concerned with a transporting means 20 for persons with reduced mobility comprising a connection device 100 adapted to ensure connection between a serum holder 10 and the transporting means 20. It is reminded that a serum holder, also called an intravenous holder, is a device used to support drug administration devices such as infusion systems, pumps and syringe pumps necessary for intravenously administrating drugs to a patient. Advantageously, transporting means 20 can take the form of a wheelchair, a wheeled stretcher, a wheeled bed or a child's pram.

In the following description, it is assumed that transporting means 20 is a wheelchair.

Figure 1:
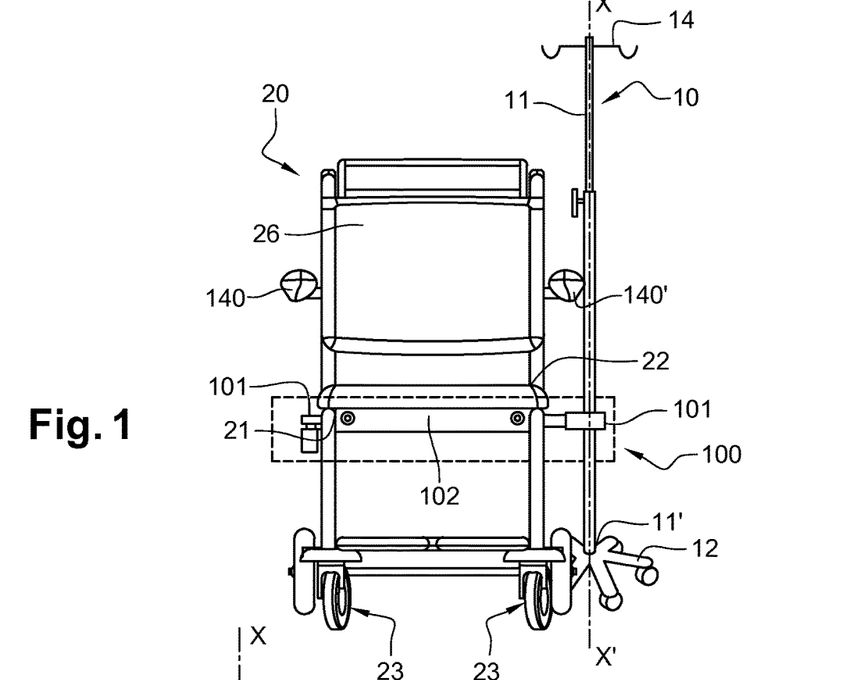
Figure 2:
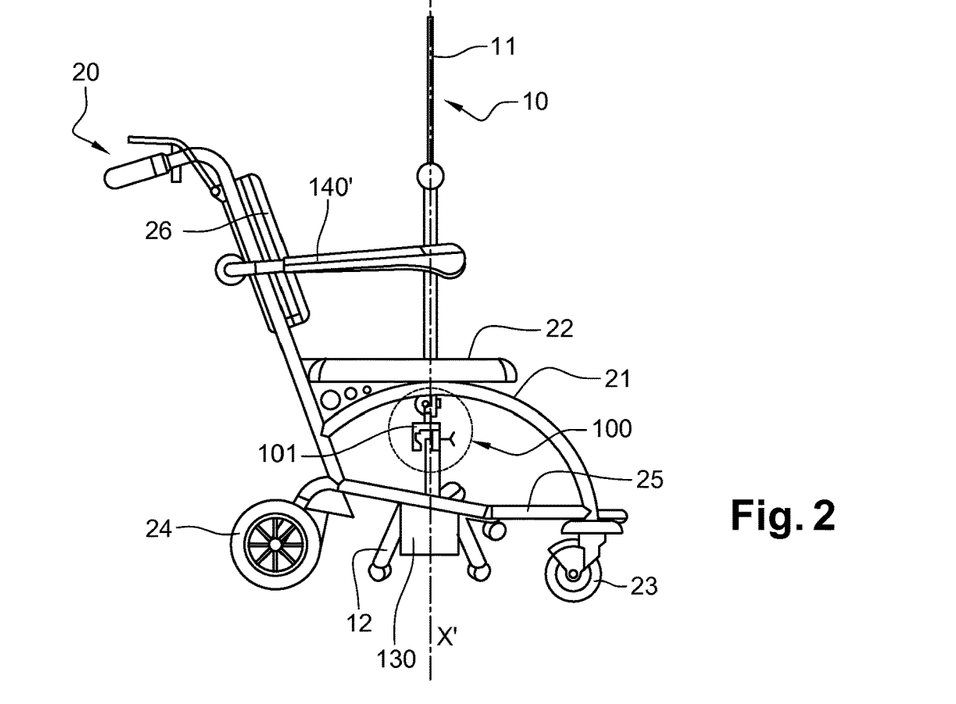

FIGS. 1 and 2 represent a front view and a side view of wheelchair 20 respectively, according to an embodiment of the invention when connected to the serum holder 10.

Serum holder 10 shown in FIGS. 1 and 2 is an example of a serum holder conventionally used in hospitals.

With reference to FIGS. 1 and 2, serum holder 10 comprises a rod 11 extending along a longitudinal axis)(X' and a wheeled support 12 attached to one end 11' of rod 11. At its other end, the rod 11 of the serum holder 10 has hooks 14 on which the different drug administration devices are suspended.

Figure 3A:
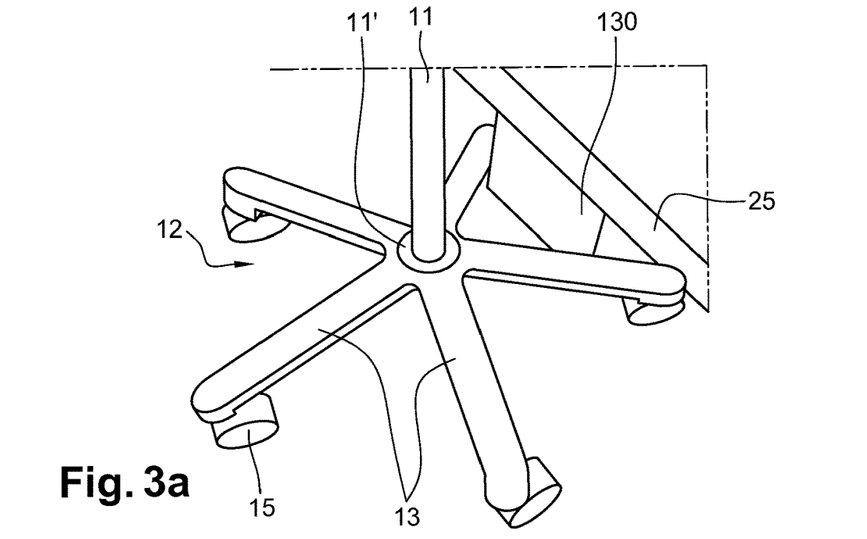

The wheeled support 12, represented more distinctively in FIG. 3a, allows the serum holder 10 to be easily moved and to accompany movements of the patient on infusion. The wheeled support 12 of the serum holder 10 is formed of a plurality of branches 13, five in number in the example illustrated in FIG. 3a, on which wheels 15 are mounted for ground contact.

In addition, the wheelchair 20 includes a chassis 21 supporting a seat 22, a backrest 26 and a first assembly of rear wheels 24 and a second assembly of front wheels 23. The first assembly of rear wheels 24 and the second assembly of front wheels 23 are separated by side cross members 25 of the chassis 21 visible in FIG. 2.

In addition, connection device 100 comprises:
a coupling element 101,
an attachment support 102,
a connection member 105,
a side stop 130,
two armrests 140, 140'.

Coupling element 101 enables the rod 11 of the serum holder 10 to be coupled to the chassis 21 of the wheelchair 20.

Figure 4A:
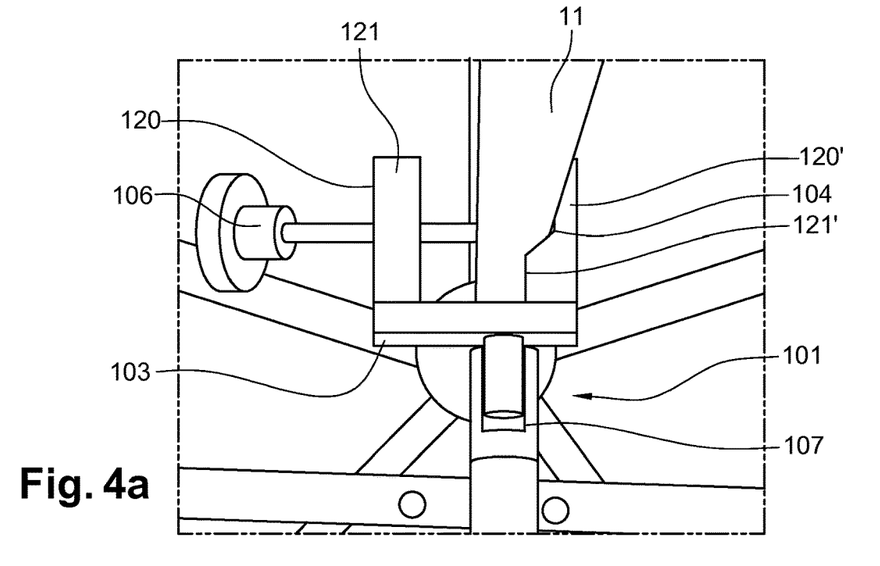
Figure 4B:
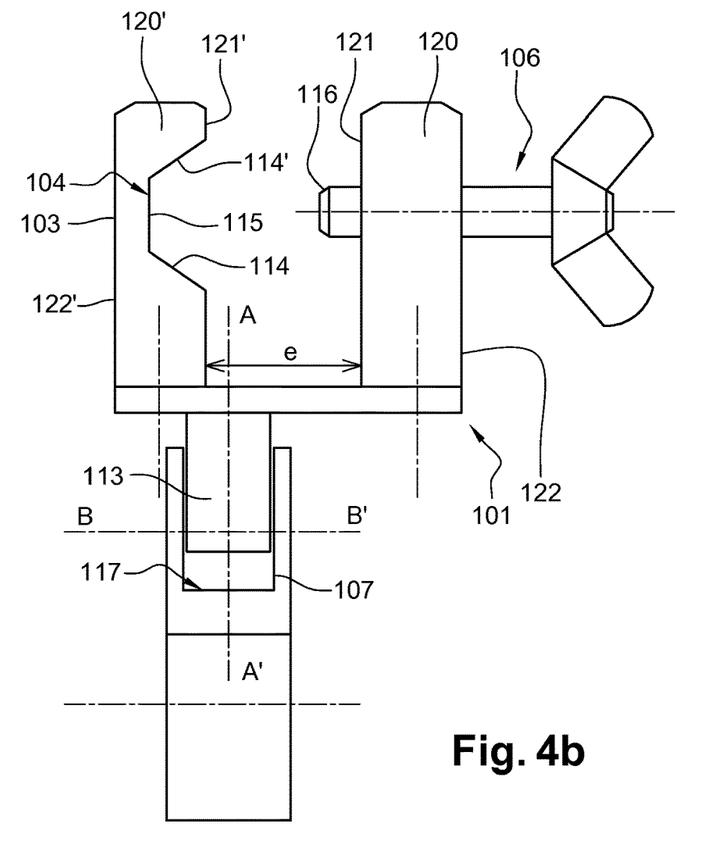

With reference to FIGS. 4a and 4b, coupling element 101 has a clamp 103 for clamping rod 11. In particular, clamp 103 has two parallel branches 120, 120' forming a jaw. According to one embodiment, clamp 103 is a one-piece element, e.g. obtained by moulding. According to another embodiment, clamp 103 is obtained by assembling the two branches 120, 120' on a connecting base. In an alternative embodiment, the connecting base and one of the branches form a one-piece component, for example obtained by machining, to which the other branch is assembled.

In addition, each branch 120, 120' of clamp 103 has an inner surface 121, 121' and an outer surface 122, 122'. Advantageously, the gap e between the inner surfaces 121, 121' of the branches 120, 120' is adapted to introduce the rod 11 of the serum holder 10. Thus, for example, the gap e is within the range [10 mm, 60 mm]. By "gap" between the branches it is meant the distance between the inner surfaces 121, 121' of the branches 120, 120' from each other. It should be noted that, according to one embodiment of the invention, the gap e may be modified by ad hoc means so as to adapt to the dimensions of the rod 11. Advantageously, sharp edges of the branches 120, 120' of clamp 103 are chamfered so as to avoid the risk of injury if a person strikes the clamp 103.

In addition, the thickness as well as material of clamp 103 are chosen to ensure that clamp 103 has sufficient strength not to be deformed and/or broken in the event of an impact or any other stress to which it may be subjected. In addition, clamp 103 is advantageously made of a material adapted not to rust, especially after many cleaning operations. Advantageously, clamp 103 is made of stainless steel.

In addition, clamp 103 has a recess 104 provided at the inner surface 121' of one of the branches 120, 120' of clamp 103, adapted to receive rod 11. The housing 104 has shape and dimensions adapted to form at least two contact points with rod 11.

Advantageously, the housing 104 has an overall "V" shape, as represented in FIG. 4b. In particular, housing 104 has two oblique surfaces 114, 114' to an intermediate surface 115 parallel to the outer surface 122' of the rod 120', with the intermediate surface 115 separating the oblique surfaces 114, 114'. Housing 104 then forms a contact point with rod 11 with each oblique surface 114 and 114'. In an alternative embodiment, housing 104 has no intermediate surface 115, which allows rods 11 of small diameter serum holder 10 to be locked between the oblique surfaces 114, 114'.

In an alternative embodiment not illustrated, the clamp 103 is in the form of a toggle or toggle clamp, i.e. a clamp with a lever which, according to its position, allows the clamp to be kept closed or open.

Advantageously, the coupling element 101 has a clamping element 106 for holding the rod 11 in the housing 104. In the embodiment of FIGS. 4a and 4b, the clamping element 106 is formed by a clamping screw adapted to be screwed into a threaded hole (not visible) passing through branch 120 opposite to branch 120' in which housing 104 is provided. The rod 11 is held in the housing 104 by screwing the clamping element 106 into the hole until the free end 116 of the clamping element 106 abuts against the rod 11 and thus exerts sufficient force to prevent the rod 11 from disengaging from the housing 104. From then on, three contact points between rod 11 and coupling element 101 are ensured by the two oblique surfaces 114 and 114' and the free end 116 of the clamping element 106. In an alternative embodiment not illustrated, the free end 116 of the clamping element 106 forms a V-shape so that the rod 11 has an additional contact point with the clamping element 106 which enables its holding in the housing 104 to be improved.

Advantageously, the free end 116 of the clamping element 106, or the entire clamping element 106, has a compressible coating, e.g. of rubber or plastic. Thus, upon screwing the clamping element 106, the coating is compressed against the rod 11, which enables the holding of the rod 11 in the housing 104 to be improved.

In addition, the attachment support 102 provides attachment of the connection device 100 to the chassis 21 of the wheelchair 20.

Figures 5A, 5B, 5C:
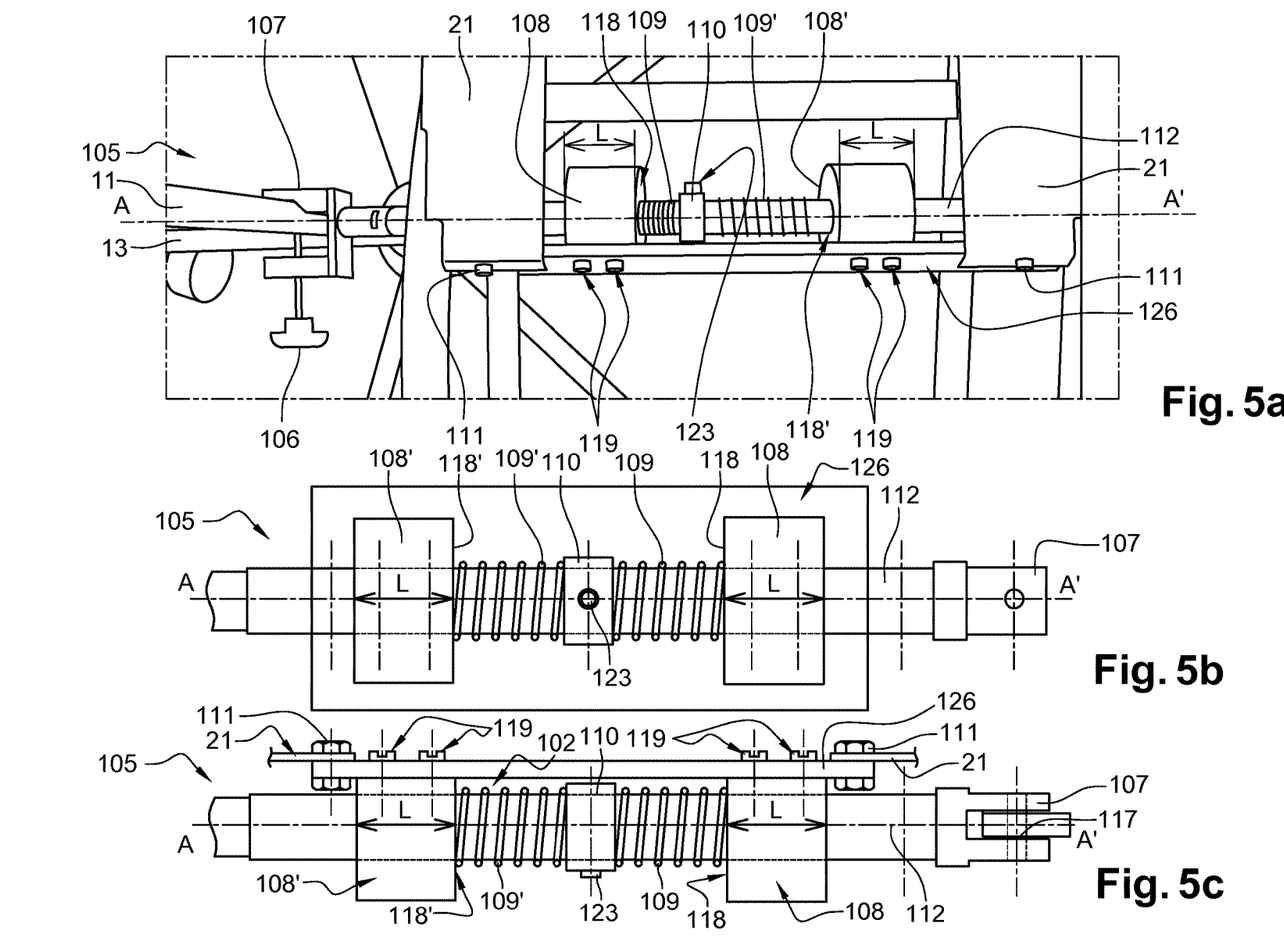

According to the embodiment illustrated in FIGS. 5a to 5c, the attachment support 102 has a rectangular plate 126 attached under the seat 22 of the wheelchair 20 by means of attachment screws 111 passing through the chassis 21 and said plate 126. In an alternative embodiment not represented, the attachment support 102 is attached to the chassis 21 by welding.

Advantageously, the thickness and material of plate 126 is chosen so as to provide it with sufficient strength so that it does not deform and/or break in use. Thus, plate 126 is for example made of stainless steel or aluminium. In addition, plate 126 has for example a thickness in the range [5 mm, 40 mm]. It is noted that the shape and dimensions of plate 126 can vary depending on the shape of the chassis 21 and/or the width of the wheelchair 20. Indeed, a wheelchair for transporting a child has a width of about 300 mm whereas a wheelchair for transporting an obese person has a width of about 800 mm.

In addition, the attachment support 102 includes at least one ring attached to plate 126. In the embodiment illustrated in FIGS. 5a, 5b and 5c, attachment support 102 has two rings 108 and 108'. In another embodiment not represented, the attachment support 102 has more than two rings. Rings 108 and 108' are attached to plate 126 with attachment screws 119, here two attachment screws 119 per ring. Of course, the rings 108, 108' can be attached to plate 126 by another attachment means.

In addition, rings 108, 108' have an internal diameter adapted to receive an axis 112 of the connection member 105 and to ensure its sliding through said rings 108, 108'. Advantageously, the rings 108, 108' are made of a material with a low coefficient of friction so as to facilitate sliding of axis 112. Advantageously, the rings 108, 108' are made of polytetrafluoroethylene, known as Teflon®. In addition, the rings 108, 108' have a length L and a thickness adapted to ensure sufficient resistance to stresses to which they are subjected. By "thickness" of the rings it is meant the distance separating their external diameter from their internal diameter. According to one embodiment, rings 108, 108' have a length L in the range [49 mm, 51 mm]. In addition, rings 108, 108' have, for example, a thickness in the range [64 mm, 66 mm].

In addition, the connection member 105 ensures coupling of the coupling element 101 to the attachment support 102. With reference to FIGS. 5a to 5c, the connection member 105 includes an axis 112 attached to the clamp 103 of coupling element 101. According to the embodiment in FIGS. 5a, 5b and 5c, the axis 112 is in the form of a tubular element extending along an axis AA'.

In the embodiment in FIG. 4b, axis 112 is solid. In this embodiment, axis 112 has a U-shaped end 107 so as to form a port 117 able to receive an end 113 of clamp 103. The end 107 of axis 112 can be obtained by machining, directly into axis 112.

In an alternative embodiment, the end 107 of axis 112 can be in the form of a tip which is attached to the end of axis 112 by means of attachment means, which avoids replacing the entire axis 112 in the event of a break at said end 107.

Advantageously, the clamp 103 is secured to the end 107 of the axis 112 by means of a through element, for example a pin, which passes through both the end 107 of the axis 112 and the end 113 of the clamp 103. By virtue of the pin, clamp 103 is pivotably mounted to axis 112. Specifically, clamp 103 is adapted to pivot about an axis BB' perpendicular to axis AA' along which axis 112 extends. Thus, when the clamp 103 is unsecured from the rod 11 of the serum holder 10, the clamp 103 naturally pivots to a vertical position facing the ground under its own weight. Such a system improves the safety of the connection device 100 by limiting risks of injury that could occur if a person were to strike the clamp 103 when it is not connected to the rod 11 of the serum holder 10. Note that clamp 103 is positioned horizontally when coupled to rod 11.

In an alternative embodiment not represented, axis 112 is hollow. In this case, the U-shaped end 107 is in the form of a tip attached to the end of axis 112 with a pin or a screw passing through axis 112 and the tip. In this alternative embodiment, clamp 103 also pivots in relation to axis 112.

In addition, the dimensions as well as the material of the axis 112 are chosen so that it has sufficient mechanical strength to withstand the stresses to which it is subjected. Advantageously, the axis 112 is of stainless steel when it is hollow and of aluminium when it is solid. In addition, the axis 112 extends over a length adapted to the dimensions of wheelchair 20, for example in the range [450 mm, 460 mm]. Naturally, the shape and dimensions of the axis 112 can vary depending on the shape of the chassis 21 and/or the width of wheelchair 20.

Connection member 105 includes a radial stop 110 attached to axis 112. According to the embodiment of FIGS. 5a, 5b and 5c, the radial stop 110 is formed by a ring surrounding the axis 112, arranged at a central portion of the axis 112. Thus, the ring has an internal diameter greater than the outer diameter of axis 112. Advantageously, the radial stop 110 is attached to the axis 112 with an attachment screw 123. Radial stop 110 and axis 112 can be formed as a single piece, e.g. by machining, or be assembled together, e.g. by welding.

In addition, the connection member 105 includes at least one return means 109 adapted to exert a return force on the coupling element 101 which directs it towards the chassis 21 of the wheelchair 20. For this purpose, the return means 109 exerts a return force on the axis 112 which is attached to the clamp 103. According to the embodiment of FIGS. 5a, 5b and 5c, the return means 109 is formed by a compression spring surrounding the axis 112. The compression spring is adapted to be compressed between one end 118 of a ring 108 and the radial stop 110 of the connection member 105. Compressing the compression spring allows the axis 112 and thus the coupling element 101 underneath the seat 22 to retract when the rod 11 is unsecured from the coupling element 101. In other words, the compression spring permanently pulls the clamp 103 underneath the seat 22 of wheelchair 20. This prevents a person walking in the proximity of wheelchair 20 from being injured by hitting the clamp 103. Advantageously, the compression spring is flexible so that the clamp 103 does not retract abruptly under the seat 22 when an operator releases the rod 11 of the clamp 103, for example of stainless steel. In addition, the compression spring, for example, has a length at rest in the range [50 mm, 60 mm].

According to one embodiment not represented, the compression spring is replaced by an assembly of cylinders which perform the same function. Advantageously, the return means 109 and 109' as well as the radial stop 110 are covered with a bellows or a cover, e.g. made of PVC, in order to protect them.

According to another embodiment, retracting the clamp 103 underneath wheelchair 20 is carried out manually by the staff or a third party accompanying the patient.

In one embodiment not illustrated, the rod 11 of the serum holder 10 is coupled to wheelchair 20 by means of two connection devices 100. In this case, the attachment support 102 of another connection device 100 is for example attached to one of the side cross members 25 of wheelchair 20.

In addition, the side stop 130 of the connection device 100 ensures that the wheeled support 12 is locked in relation to the chassis 21 of the wheelchair 20 and that the serum holder 10 is positioned laterally in relation to the wheelchair 20. For this purpose, the side stop 130 is attached to at least one of the side cross members 25 of the wheelchair 20, between a front wheel 23 and a rear wheel 24 of the wheelchair 20.

Figure 3B:
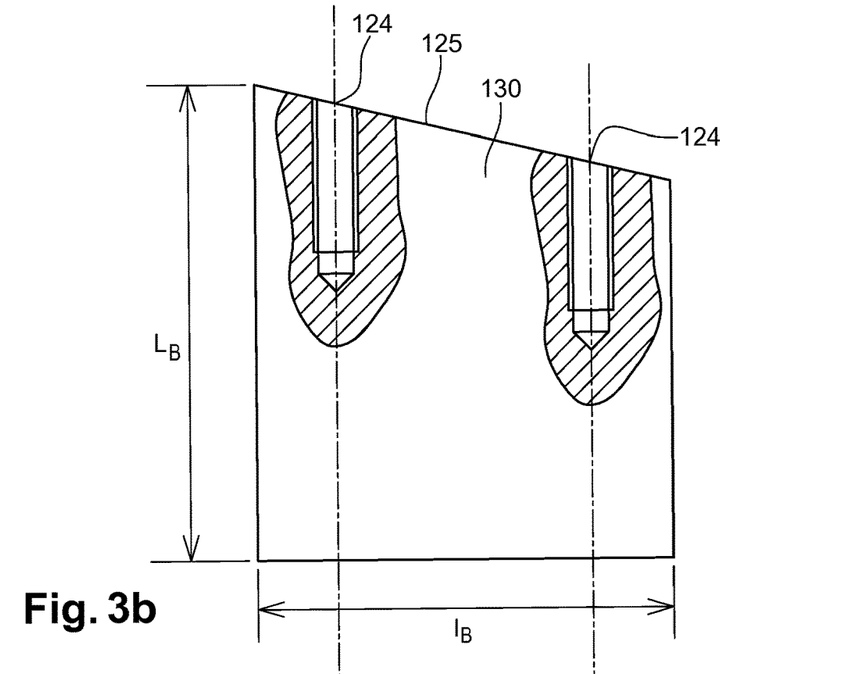
Figure 3C:
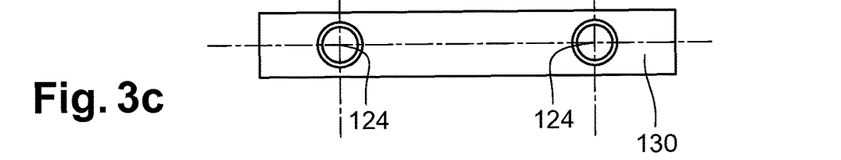

Referring to FIGS. 3a, 3b and 3c, the side stop 130 has an overall rectangular shape. In particular, the side stop 130 has an oblique upper side 125 which is adapted to follow the tilt of the side cross member 25 of wheelchair 20 on which the side stop 130 is mounted.

In addition, the side stop 130 has a length $L_B$ and width $I_B$ adapted to lock the side stop 130 between two branches 13 of the wheelchair support 12. The length $L_B$ of the side stop 130 can vary depending on the tilt of the side cross member 25. The side stop 130 has for example a length $L_B$ in the range [30 mm, 300 mm] and a width $I_B$ in the range [100 mm, 180 mm].

Attaching the side stop 130 to the side cross member 25 by means of attachment screws 124, in this case two attachment screws, passing through the side cross member 25 and the side stop 130 in the direction of the length $L_B$ of the side stop 130. Advantageously, the thickness of the side stop 130 is selected so that the attachment screws 124 can be introduced into the side stop.

Advantageously, the side stop 130 is made of a material for absorbing noise that can be generated by contacting the branches 13 of the wheeled support 12 with the side stop 130 and to prevent rusting, especially after several cleaning operations. The side stop 130 is, for example, made of polytetrafluoroethylene, known as Teflon®.

In an alternative embodiment not illustrated, the side stop 130 is made of a metal material such as steel or aluminium. Advantageously, the side stop 130 can then be welded to the side cross member 25 of wheelchair 20.

In addition, the thickness as well as the material of the end stop 130 are chosen so that the end stop 130 has sufficient mechanical strength to withstand stresses to which it is subjected. By way of example, the thickness of the side stop 130 is in the range [10 mm, 40 mm].

Advantageously, the armrests 140, 140' of the connection device 100 form a support for a patient's elbow or branch while also providing lock for the rod 11 of the serum holder 10. The armrests 140, 140' are attached to the chassis 21 of the wheelchair 20, for example, by means of attachment screws passing through the chassis 21.

Advantageously, the armrests 140, 140' are removable. According to the embodiment illustrated in FIG. 1, connection device 100 includes two armrests 140, 140'. In an alternative embodiment, the connection device 100 has only one arm rest.

Additionally, according to a second embodiment, connection device 100 25 includes:
  two coupling elements 101,
  an attachment support 102,
  a connection member 105,
  two side stops 130,
  two armrests 140, 140'.

Such an embodiment is particularly advantageous in that it allows two serum holders 10 to be connected to the same wheelchair 20 from a single connection device 100.

In this embodiment, a side stop 130 is attached to each side cross member 25 of the wheelchair 20, so that the wheeled support 12 of each serum holder 10 is locked in relation to the chassis 21 of the wheelchair 20, in other words, in addition to the side stop 130 described previously, an additional side stop 130 is attached to the other side cross member 25 in order to lock an additional serum holder 10.

Further, as can be seen in FIG. 1, a coupling element 101 is attached at each end 107 of axis 112 of the connection member 105. Thus, in addition to the coupling element 101, previously described, an additional coupling element 130 is attached to the other end 107 of axis 112 of the connection member 105. In other words, two clamps 103 and two clamping elements 106 are arranged on either side of axis 112.

Additionally, in this embodiment, the connection member 105 has two return means 109 and 109' as illustrated in FIGS. 5a, 5b and 5c. The return means 109 and 109' are formed by compression springs arranged on either side of the radial stop 110. Each compression spring is adapted to be compressed between one of the rings 108, 108' and the radial stop 110 so as to exert a return force on each clamp 103. The rod 11 of each serum holder 10 is locked against one of the armrests 140, 140' of the wheelchair 20.

The embodiments described above are in no way limiting so that modifications can be made thereto without departing from the scope of the invention.

The invention claimed is:

1. A transporting system for persons with reduced mobility comprising a chassis having two side cross members connecting a first assembly of rear wheels to a second assembly of front wheels, said transporting system further comprising a connection device for connecting to a serum holder to ensure a lateral side positioning of the serum holder with respect to the transporting system, said serum holder comprising a rod and a wheeled support attached to one end of said rod, the connection device comprising:
  an attachment support attached to the chassis,
  a coupling element for being secured to the rod, the coupling element comprising:
    a clamp having a housing adapted to receive the rod and,
    a clamping element adapted to hold the rod in the housing,
  a connection member for connecting the coupling element to the attachment support,
  a side stop attached to one of the side cross members of the chassis, said side stop being constructed and arranged to ensure locking of the wheeled support with respect to the chassis.

2. The transporting system according to claim 1, wherein the clamp comprises two branches each having an inner surface, the housing being provided in an inner surface of one of the two branches.

3. The transporting system according to claim 1, wherein the housing is constructed and arranged to form at least two contact points between the housing and the rod.

4. The transporting system according to claim 1, wherein the housing has a V shape.

5. The transporting system according to claim 1, wherein the attachment support comprises:
  a plate for being directly attached to the chassis of the transporting system,
  at least one ring attached to said plate.

6. The transporting system according to claim 1, wherein the connection member comprises at least one return means for returning the coupling element to the chassis of the transporting system.

7. The transporting system according to claim 5, wherein the connection member includes:
  an axis attached to the clamp of the coupling element, said axis being slidably mounted through said at least one ring of the attachment support,
  a radial stop attached to said axis.

8. The transporting system according to claim 7, wherein the connection member comprises at least one return means for returning the coupling element to the chassis of the transporting system, and wherein the return means is formed by a compression spring surrounding the axis, said compression spring being adapted to be compressed between one end of said at least one ring and the radial stop.

9. The transporting system according to claim 1, wherein the side stop has a shape and dimensions adapted to lock two branches of the wheeled support of the serum holder.

10. The transporting system according to claim 1, wherein the connection device comprises at least one armrest attached to the chassis, said at least one armrest being constructed and arranged to ensure locking of the rod of the serum holder relative to said chassis.

11. The transporting system according to claim 1, wherein the connection device comprises:
  an additional coupling element attached to the connection member, said additional coupling element being for being secured to the rod of an additional serum holder and including:
    a clamp having a housing adapted to receive a rod of the additional serum holder and,
    a clamping element adapted to hold the rod of the serum holder in the housing,
  an additional side stop attached to the other side cross member of the chassis, said side stop being constructed and arranged to ensure locking of a wheeled support of the additional serum holder relative to the chassis and to ensure lateral side positioning of the additional serum holder relative to the transporting system.

12. The transporting system according to claim 11, further comprising an additional armrest attached to the chassis, said additional armrest being constructed and arranged to ensure locking of the rod of the serum holder relative to said chassis.

13. The transporting system according to claim 1, wherein the transporting system is one of:
 a wheelchair,
 a wheeled stretcher,
 a wheeled bed, and
 a pram.

14. An assembly for connecting a serum holder to the transporting system for persons with reduced mobility according to claim 1, said connection assembly comprising:
 the transporting system,
 the serum holder including a rod and a wheeled support attached to one end of said rod,
 the transporting system being coupled to the serum holder by the connection device of said transporting system.

* * * * *